United States Patent [19]

Huff

[11] Patent Number: 4,970,330
[45] Date of Patent: * Nov. 13, 1990

[54] HALOGENATED ESTERS

[75] Inventor: Roger K. Huff, Wokingham, England

[73] Assignee: Imperial Chemical Industries PLC, London, England

[*] Notice: The portion of the term of this patent subsequent to Jan. 15, 1997 has been disclaimed.

[21] Appl. No.: 454,863

[22] Filed: Dec. 30, 1982

Related U.S. Application Data

[60] Continuation of Ser. No. 242,415, Mar. 10, 1981, Pat. No. 4,378,316, which is a division of Ser. No. 60,165, Jul. 24, 1979, Pat. No. 4,330,675, which is a division of Ser. No. 869,615, Jan. 16, 1978, Pat. No. 4,183,948.

[30] Foreign Application Priority Data

Jan. 24, 1977 [GB] United Kingdom ............ 2763
Mar. 23, 1977 [GB] United Kingdom ............ 12210
Sep. 2, 1977 [GB] United Kingdom ............ 36714
Sep. 2, 1977 [GB] United Kingdom ............ 36715

[51] Int. Cl.$^5$ ............... C07C 69/743; C07C 69/747; C07C 255/15
[52] U.S. Cl. ............................. 558/407; 560/124
[58] Field of Search ............ 260/465 D; 560/124; 558/407

[56] References Cited

U.S. PATENT DOCUMENTS 4,183,948  1/1980  Huff ................................ 424/304
4,332,815  6/1982  Engel .............................. 424/274

Primary Examiner—Richard L. Raymond
Attorney, Agent, or Firm—Cushman, Darby & Cushman

[57] ABSTRACT

A compound of the formula

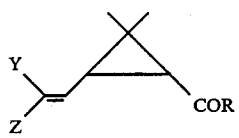

wherein one of Y and Z is a perhaloalkyl group having 1 to 2 carbon atoms and the other is halogen or methyl; and R is $OR^1$ in which $R^1$ represents a phenoxybenzyl group optionally substituted in the alpha position by a cyano or ethynyl group.

1 Claim, No Drawings

HALOGENATED ESTERS

This is a continuation of application Ser. No. 242,415, filed Mar. 10, 1981, (now U.S. Pat. No. 4,378,310) which is a division of Ser. No. 60,165, filed July 24, 1979 (now U.S. Pat. No. 4,330,675), which is a division of Ser. No. 869,615, filed Jan. 16, 1978 (now U.S. Pat. No. 4,183,948).

This invention relates to novel cyclopropane derivatives useful as insecticides, to processes for their preparation, to compositions comprising them and to methods of combating insect and similar invertebrate pests using them Certain naturally occurring esters of cyclopropane carboxylic acids have long been known to possess insecticidal properties, but these compounds have been too easily degraded by ultra violet light to be of much use in agriculture. Several groups of synthetic compounds based on cyclopropane carboxylic acids (for example those disclosed in British patent specifications nos 1,243,858 and 1,413,491) have been evaluated in an attempt to discover compounds of sufficient light stability for use as general agricultural insecticides.

We have now discovered that compounds according to the general formula:

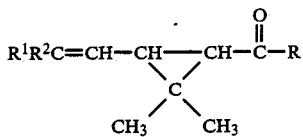

wherein $R^1$ and $R^2$ are both haloalkyl groups containing 1 or 2 atoms or in which one of $R^1$ and $R^2$ is such a haloalkyl group and the other is a halogen atom or a methyl group, and in which R is a phenoxybenzyloxy group optionally substituted in the α-position by a cyano or ethynyl group have very good insecticidal properties combined with good resistance to light degradation, and that similar compounds wherein R is a hydroxy group or an alkoxy- group containing up to 6 carbon atoms, or a halogen atom are useful as intermediates for the preparation of insecticides. Where R is a phenoxybenzyloxy or α-substituted phenoxybenzyloxy group it is preferably a 3-phenoxybenzyloxy or α-substituted 3-phenox-vbenzyloxy group.

In one aspect therefore the present invention provides compounds according to the general formula:

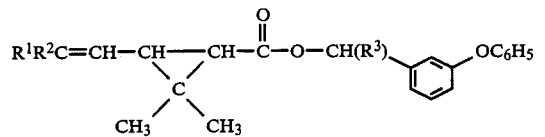 (I)

wherein one of $R^1$ and $R^2$ represents a group of formula:

where W represents an atom of hydrogen, fluorine or chlorine and m has the value one or two, and the other of $R^1$ and $R^2$ represents an atom of fluorine, chlorine or bromine or a group of formula:

where each of X, Y and Z independently represents an atom of hydrogen, fluorine or chlorine, and $R^3$ represents an atom of hydrogen or the cyano or ethynyl group.

One preferred group of compounds within the invention are those according to the general formula I given above in which one of $R^1$ and $R^2$ represents a group of formula:

where W represents an atom of hydrogen, fluorine or chlorine, and the other of $R^1$ and $R^2$ represents a group of formula:

where X, Y and Z are as defined above, and $R^3$ represents an atom of hydrogen or the cyano group. Within this preferred group of compounds those which are particularly preferred are those wherein $R^1$ and $R^2$ are both trifluoromethyl groups.

Another preferred group of compounds within the invention are those according to the general formula I given above in which one of $R^1$ and $R^2$ represents a group of formula:

where W represents an atom of hydrogen, fluorine or chlorine, and the other of $R^1$ and $R^2$ represents a fluorine, chlorine, or bromine atom, and $R^3$ represents an atom of hydrogen or the cyano group. Especially preferred compounds within this group are those wherein one of $R^1$ and $R^2$ represents the trifluoromethyl group and the other represents a chlorine or bromine atom.

It will be appreciated by those skilled in the art that the compounds represented by formula I are capable of existing in various geometrical and stereoisomeric forms. Thus there may be cis and trans isomers arising from the substitution pattern of the cyclopropane ring, and E- and Z-isomers arising from the substituted vinyl group when $R^1$ is not the same as $R^2$. In addition two of the three carbon atoms of the cyclopropane are capable of existing in either R- or S-configurations since they are asymmetrically substituted, and when $R^3$ is not hydrogen the carbon atom to which it is attached is also capable of existing in either the R- or S- configuration.

Thus for a compound according to formula I where $R^1$ and $R^2$ are the same and $R^3$ is hydrogen, there are four isomeric possibilities, arising from the cyclopropane ring substitution. These may be named by reference to their absolute configuration as (1R,3R), (1R,3S), (1S,3S) and (1S,3R). When $R^3$ is not hydrogen there are eight possible isomers since each of the four possible cyclopropane ring configurations must exist in two forms, one corresponding to the S-configuration and one to the R-configuration of the carbon atom bearing the $R^3$ group. Alternatively if $R^3$ is hydrogen, and $R^1$ is not the same as R² there are again eight isomeric possibilities since each of the four possible cyclopropane ring configurations must exist in two forms, one corresponding to the Z-configuration and one to the E-configuration of the vinyl group.

Finally when R¹ is not the same as R², and R³ is not hydrogen, each compound may exist in sixteen isomeric forms.

In Table I there are listed compounds according to the invention. Each of the compounds listed is a racemic mixture of (+) and (−) isomers, although a distinction is made between cis and trans substitution on the cyclopropane ring and E- and Z-substitution in the vinyl group where this is present.

The compounds of Table I all conform to the following formula:

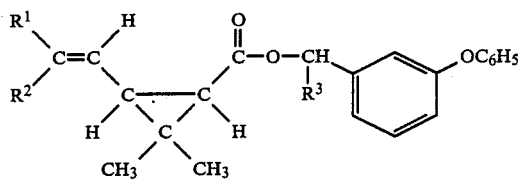

TABLE I

| COMPOUND NO | R¹ | R² | R³ | CONFIGURATION OF CYCLOPROPANE RING SUBSTITUENTS |
|---|---|---|---|---|
| 1 | CF₃ | CF₃ | CN | cis |
| 2 | CF₃ | CF₃ | CN | trans |
| 3 | CF₃ | CF₃ | H | cis |
| 4 | CF₃ | CF₃ | H | trans |
| 5 | CHF₂ | CHF₂ | H | cis |
| 6 | CHF₂ | CHF₂ | H | trans |
| 7 | CHF₂ | CHF₂ | CN | cis |
| 8 | CHF₂ | CHF₂ | CN | trans |
| 9 | CF₂Cl | CF₂Cl | H | cis |
| 10 | CF₂Cl | CF₂Cl | H | trans |
| 11 | CF₂Cl | CF₂Cl | CN | cis |
| 12 | CF₂Cl | CF₂Cl | CN | trans |
| 13 | CF₃ | CF₃ | C≡CH | cis |
| 14 | CF₃ | CF₃ | C≡CH | trans |
| 15 | CHF₂ | CF₃ | CN | cis |
| 16 | CF₃ | CHF₂ | CN | cis |
| 17 | CHF₂ | CF₃ | CN | trans |
| 18 | CF₃ | CHF₂ | CN | trans |
| 19 | CH₃ | CF₃ | CN | cis |
| 20 | CF₃ | CH₃ | CN | cis |
| 21 | CH₃ | CF₃ | CN | trans |
| 22 | CF₃ | CH₃ | CN | trans |
| 23 | CH₃ | CF₃ | H | cis |
| 24 | CF₃ | CH₃ | H | cis |
| 25 | CH₃ | CF₃ | H | trans |
| 26 | CF₃ | CH₃ | H | trans |
| 27 | CHF₂ | CF₂Cl | CN | cis |
| 28 | CF₂Cl | CHF₂ | CN | cis |
| 29 | CHF₂ | CF₂Cl | CN | trans |
| 30 | CF₂Cl | CHF₂ | CN | trans |
| 31 | CF₃ | Cl | CN | cis |
| 32 | Cl | CF₃ | CN | cis |
| 33 | CF₃ | Cl | CN | trans |
| 34 | Cl | CF₃ | CN | trans |
| 35 | CF₃ | Cl | H | cis |
| 36 | Cl | CF₃ | H | cis |
| 37 | CF₃ | Cl | H | trans |
| 38 | Cl | CF₃ | H | trans |
| 39 | CF₂Cl | Cl | H | cis |
| 40 | Cl | CF₂Cl | H | cis |
| 41 | CF₂Cl | Cl | H | trans |
| 42 | Cl | CF₂Cl | H | trans |
| 43 | CF₂Cl | Cl | CN | cis |
| 44 | Cl | CF₂Cl | CN | cis |
| 45 | CF₂Cl | Cl | CN | trans |
| 46 | Cl | CF₂Cl | CN | trans |
| 47 | CF₂Cl | F | CN | cis |
| 48 | CF₂Cl | F | CN | trans |
| 49 | CF₂Cl | F | H | cis |
| 50 | CF₂Cl | F | H | trans |
| 51 | ClCF₂CF₂ | Cl | CN | cis |
| 52 | ClCF₂CF₂ | Cl | CN | trans |
| 53 | CF₃CF₂ | Cl | CN | trans |
| 54 | CF₃ | Br | CN | cis |
| 55 | Br | CF₃ | CN | cis |
| 56 | CF₃ | Br | CN | trans |
| 57 | Br | CF₃ | CN | trans |
| 58 | CF₃ | Cl | C≡CH | cis |
| 59 | Cl | CF₃ | C≡CH | cis |
| 60 | CF₃ | Cl | C≡CH | trans |

TABLE I-continued

| COMPOUND NO | $R^1$ | $R^2$ | $R^3$ | CONFIGURATION OF CYCLOPROPANE RING SUBSTITUENTS |
|---|---|---|---|---|
| 61 | Cl | $CF_3$ | C≡CH | trans |

Particularly useful compounds of formula I according to the invention include:

(+)-α-cyano-3-phenoxybenzyl (+)-cis/trans-3-(2-chloro-3,3,3-trifluoroprop-1-en-1-yl)-2,2-dimethylcyclopropane carboxylate, (+)-α-cyano-3-phenoxybenzyl (+)-cis/trans-3-(3,3,3-trifluoro-2-trifluoromethylprop-1-en-1-yl)-2,2-dimethylcyclopropane carboxylate, (+)-α-cyano-3-phenoxybenzyl (+)-cis/trans-3-(3-chloro2,3,3-trifluoroprop-1-en-1-yl)-2,2-dimethylcyclopropane carboxylate, (+)-α-cyano-3-phenoxybenzyl (+)-cis/trans-3-(3-bromo-3,3,3-trifluoroprop-1-en 1-yl)-2,2-dimethylcyclopropane carboxylate, 3-phenoxybenzyl (+)-cis/trans-3-(2-chloro-3,3,3-trifluoroprop-1-en-1-yl)-2,2-dimethylcyclopropane carboxylate, and 3-phenoxybenzyl- (+)-cis/trans-3-(3,3,3-trifluoro-2-trifluoromethylprop-1-en-1-yl)-2,2-dimethylcyclopropane carboxylate.

The compounds of the invention according to Formula I are esters and may be prepared by conventional esterification processes, of which the following are examples.

(a) An acid of formula:

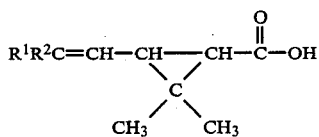

where $R^1$ and $R^2$ have any of the meanings given hereinabove, may be reacted directly with an alcohol of formula:

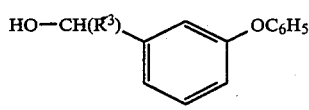

where $R^3$ represents the hydrogen atom, or the cyano or ethynyl group, the reaction preferably taking place in the presence of an acid catalyst, for example, dry hydrogen chloride.

(b) An acid halide of formula:

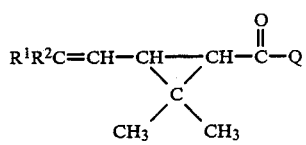

where Q represents a halogen atom, preferably a chlorine atom, and $R^1$ and $R^2$ have any of the meanings given hereinabove, may be reacted with an alcohol of formula:

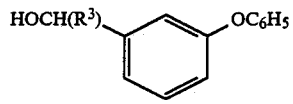

wherein $R^3$ represents the hydrogen atom or the cyano or ethynyl group, the reaction preferably taking place in the presence of a base, for example, pyridine, alkali metal hydroxide or carbonate, or alkali metal alkoxide. As an alternative when $R^3$ is to be the cyano group, a mixture of alkali metal cyanide and 3-phenoxybenzaldehyde may be employed in place of α-cyano-3-phenoxybenzyl- alcohol.

(c) An acid of formula:

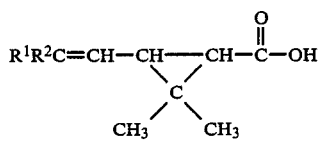

or, preferably, an alkali metal salt thereof, may be reacted with a halide of formula:

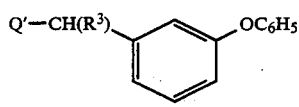

where Q' represents a halogen atoms preferably the chlorine atom, and $R^3$ represents the hydrogen atom, or the cyano or ethynyl group, or with the quaternary ammonium salts derived from such halides with tertiary amines, for example pyridine, or trialkyl amines such as triethylamine.

(d) A lower alkyl ester of formula:

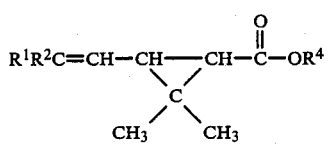

where $R^4$ represents a lower alkyl group containing up to six carbon atoms, preferably the methyl or ethyl group, and $R^1$ and $R^2$ have any of the meanings given hereinabove, is heated with an alcohol of formula:

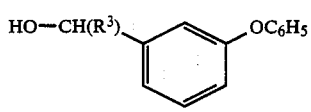

to effect a transesterification reaction. Preferably the process is performed in the presence of a suitable catalyst, for example, an alkali metal alkoxide, such as sodium methoxide, or an alkylated titanium derivative, such as tetramethyl titanate.

All of these conventional processes for the preparation of esters may be carried out using solvents and diluents for the various reactants where appropriate, and may be accelerated or lead to higher yields of product when performed at elevated temperatures or in the presence of appropriate catalysts, for example phase-transfer catalysts.

The preparation of individual isomers may be carried out in the same manner but commencing from the corresponding individual isomers of compounds of formula II. These may be obtained by conventional isomer separation techniques from mixtures of isomers. Thus cis and trans isomers may be separated by fractional crystallisation of the carboxylic acids or salts thereof, whilst the various optically active species may be obtained by fractional crystallisation of salts of the acids with optically active amines, followed by regeneration of the optically pure acid.

The optically pure isomeric form of the acid (or its equivalent acid chloride or ester) may then be reacted with 3-phenoxybenzyl alcohol to produce the compounds of formula I in the form of an individually pure isomer thereof. In the case of α-cyano-3-phenoxybenzyl alcohol the product will be a mixture of two isomers since it is not possible to react optically pure α-cyano-3-phenoxybenzyl alcohol with the acid or its equivalent without racemisation of the alcohol occurring. Typical products of this procedure include:

(+)-α-cyano-3-phenoxybenzyl(1R, 3R)-3-(3,3,3-trifluoro-2-trifluoromethylprop-1en-1-yl)-2,2-dimethylcyclopropane carboxylate, and (+)-α-cyano-3-phenoxybenzyl (1R,3S)-3-(2-chloro-3,3,3-trifluoroprop-1-en-1-yl)-2,2-dimethylcyclopropane carboxylate.

These compounds are believed to be especially useful as insecticides.

The preparation of single isomers of these compounds may be achieved by preparing the optically pure acid chloride and reacting it with (+)-3-phenoxymandelanide to give the corresponding (+)-α-carboxamido ester The two isomeric esters may be separated by fractional crystallisation, and individually- subjected to dehydration to the corresponding α-cyano-3-phenoxybenzyl ester. In this way the following single isomers may be obtained.

(S)-α-cyano-3-phenoxybenzyl (1R,3R)-3-(3,3,3-trifluoro-2-trifluoromethylprop-1-en-1-yl)-2,2-dimethylcyclopropane carboxylate, and (S)-α-cyano-3-phenoxybenzyl (1R,3S)-3-(2-chloro-3,3,3-trifluoroprop-1-en-1-yl)-2,2-dimethylcyclopropane carboxylate, which are believed to be the insecticidally most effective isomers of those particular compounds.

The various cyclopropane compounds referred to hereinabove as being useful as intermediates in the processes by which the invention compounds of Formula I may be prepared are themselves novel compounds.

In further aspect therefore the present invention provides compounds according to the general formula:

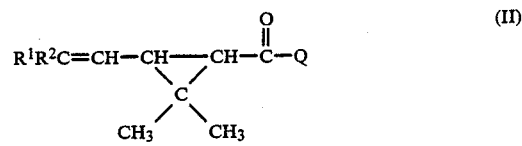

wherein one of $R^1$ and $R^2$ represents a group of formula:

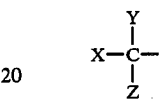

where W represents an atom of hydrogen, fluorine or chlorine and m has the value one or two, and the other of $R^1$ and $R^2$ represents an atom of fluorine, chlorine or bromine or a group of formula:

$$X-\underset{\underset{Z}{|}}{\overset{\overset{Y}{|}}{C}}-$$

where each of X, Y and Z independently represents an atom of hydrogen, fluorine or chlorine, and Q represents the hydroxy group, a lower alkoxy group containing up to six carbon atoms, or the chlorine or bromine atom.

One preferred group of intermediates within the invention are those according to the general formula II given above in which one of $R^1$ and $R^2$ represents a group of formula:
$$WCF_2-$$

where W represents an atom of hydrogen, fluorine or chlorine, and the other of $R^1$ and $R^2$ represents a group of formula:

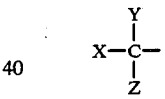

where X, Y and Z are as defined above, and Q represents the hydroxy group, a lower alkoxy group containing from one to three carbon atoms, or the chlorine or bromine atom. Within this preferred group of compounds those which are particularly preferred are those wherein $R^1$ and $R^2$ are both trifluoromethyl groups.

Another preferred group of intermediates within the invention are those according to the general formula II given above in which one of $R^1$ and $R^2$ represents a group of formula:

$$WCF_2-$$

where W represents an atom of hydrogen, fluorine or chlorine and the other of $R^1$ and $R^2$ represents a fluorine, chlorine, or bromine atom, and Q represents the hydroxy group, a lower alkoxy group containing from one to three carbon atoms, or the chlorine or bromine atom. Especially preferred compounds within this group are those wherein one of $R^1$ and $R^2$ represents the trifluoromethyl group and the other represents a chlorine or bromine atom.

The compounds represented by formula II are also capable of existing in various geometrical and stereoisomeric forms in the same way as the compounds of formula I. Thus there may be cis and trans isomers arising from the substitution pattern of the cyclopropane ring, and E- and Z-isomers arising from the substituted vinyl group when $R^1$ is not the same as $R^2$. In addition two of the three carbon atoms of the cyclopropane are capable of existing in either R- or S-configurations since they are asymmetrically substituted.

Examples of specific intermediate compounds according to the invention include those represented by the following general formula:

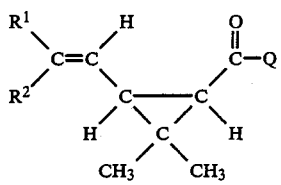

wherein $R^1$ and $R^2$ have the specific meanings given in Table I hereinabove for the corresponding compounds of formula I and wherein Q represents a chlorine atom, a hydroxy group or an ethoxy group.

The compounds of formula II wherein Q is hydroxy may be obtained by hydrolysis of the compounds of formula II wherein Q is lower alkoxy, and may be converted to the compounds of formula II wherein Q is chloro or bromo by reaction with for example: thionyl chloride or thionyl bromide respectively. All of the compounds of formula II may be used either directly or indirectly to prepare the insecticidally active esters of formula I, as described hereinabove.

The compounds of formula II wherein Q is lower alkoxy may be prepared by a variety of processes. One method involves reacting a diene of formula:

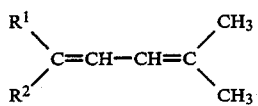

with a lower alkyl ester of diazoacetic acid. This gives rise to the required compound of formula II directly. The process is conveniently conducted using an excess of the diene as a solvent for the alkyl diazoacetate in the presence of a metallic catalyst, for example powdered copper or copper bronze.

In a variation of the above process a compound of formula III may be obtained by the reaction of the unsaturated alcohol of formula IV with a lower alkyl diazoacetate, and may be converted to a compound of formula II where Q is lower alkoxy by dehydration with a chemical dehydrating agent, for example, phosphorus pentoxide.

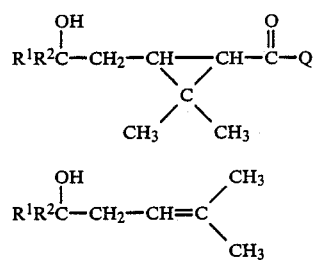

This variant of the diazoacetate process is not applicable to the preparation of compounds wherein one of $R^1$ and $R^2$ is a halogen atom, but is very useful for the preparation of compounds where $R^1$ and $R^2$ are both trifluoromethyl groups, or wherein one of $R^1$ and $R^2$ is trifluoromethyl and the other is difluoromethyl. In a yet further aspect the invention provides compounds of formula:

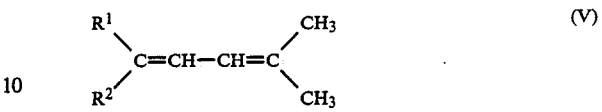

wherein $R^1$ and $R^2$ are as defined hereinabove for the compounds of formula I, and compounds of formula:

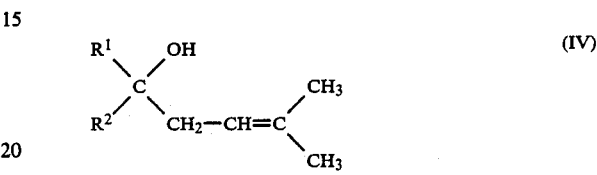

wherein $R^1$ is trifluoromethyl, and $R^2$ is trifluoromethyl or difluoromethyl.

The compounds of formula IV may be obtained by reacting a ketone of formula:

with 3-methylbut-1-ene, preferably under pressure. The corresponding compounds of formula V may be obtained by dehydration, with e.g. phosphorus pentoxide, of the compounds of formula IV.

The compounds of formula V wherein $R^1$ and $R^2$ are both haloalkyl groups or wherein one of $R^1$ and $R^2$ is a haloalkyl group and the other is a methyl group may also be obtained by reacting the corresponding ketone of formula:

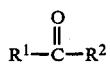

with the ylid obtained by treating a 3,3-dimethylallyl triphenylphosphonium halide, preferably the chloride or bromide, with a suitable dehydrohalogenating agent, for example an alkyllithium compound such as n-butyllithium. The phosphonium halide may be obtained by reacting triphenyl phosphine with a 3,3-dimethylallyl halide. Dienes which may be obtained by this process include those of formula V wherein $R^1$ and $R^2$ are as defined in the following table:

| $R^1$ | $R^2$ |
|---|---|
| $CF_3$ | $CF_3$ |
| $CHF_2$ | $CHF_2$ |
| $CF_3$ | $CHF_2$ |
| $CF_3$ | $CH_3$ |
| $CF_2Cl$ | $CF_2Cl$ |
| $CHF_2$ | $CF_2Cl$ |

Examples of compounds of formula IV are 5-hydroxy-2-methyl-6,6,6-trifluoro-5-trifluoromethylhex-2-ene and 5-hydroxy-2-methyl-6,6-difluoro-5-trifluoromethylhex-2ene, and these may be dehydrated to 2-methyl-6,6,6-trifluoro5-trifluoromethylhexa-2,4-diene and 2-methyl-6,6-difluoro5-trifluoromethylhexa-2,4-diene as examples of compounds of formula V.

Another method of preparing the compound-s of formula II where Q is alkoxy involves the base induced ring closure of a compound of formula:

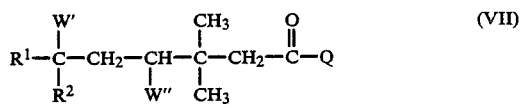 (VII)

wherein $R^1$ and $R^2$ have any of the meanings given above, Q is alkoxy, and W' and W''' are each either fluorine, chlorine or bromine, provided that W' is bromine when $R^2$ is bromine.

Suitable bases for carrying out the process include tertiary amines, for example pyridine, triethylamine, diethylaniline and N-methylpiperidine, and also alkali metal lower alkoxides, that is those containing up to six carbon atoms, for example sodium methoxide, sodium ethoxide, and sodium and potassium t-butoxide. The step is conveniently carried out in a diluent or solvent for the reactant and the base. A particularly convenient manner of conducting this process is to treat a solution of the compound of formula III in an alcohol corresponding to the alkali metal alkoxide being used for a period of from 0.5 to 20 hours.

At least two moles of base are required to convert the compounds of formula VII to the compounds of formula II where R is alkoxy, and this involves two separate stages, cyclisation and β-elimination of hydrogen halide, but it is not clear in what order these two stages proceed or if they proceed simultaneously.

When the process is conducted using only one molar equivalent of base three different products are obtained corresponding to the following formulae:

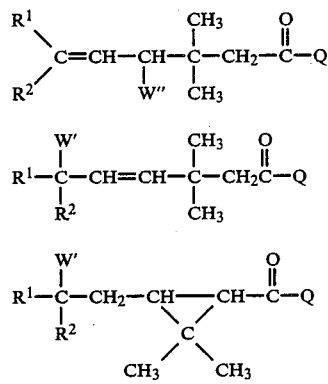

Each of these species on treatment with a further molar equivalent of base gives the compound of formula III, and in a further aspect therefore the invention provides a process for preparing the compounds of formula II where Q is alkoxy by treating a compound of formula A, B or C with at least one molar equivalent of a base. Although the process may be used for the preparation of all of the compounds of formula II where Q is alkoxy it is particularly useful for the preparation of compounds wherein one of $R^1$ and $R^2$ is a halogen atom.

The compounds of formula VII useful as intermediates in the preparation of the compounds of formula II may be prepared by reacting a compound of formula:

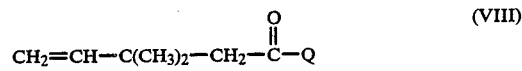 (VIII)

wherein Q is alkoxy, with a compound of formula:

 (IX)

wherein $R^1$, $R^2$, W' and W'' have any of the meanings given hereinbefore, in the presence of a free radical initiator. This may be a physical initiator such as irradiation with a suitable e.g ultra violet, light source, or a conventional chemical free radical catalyst, such as e.g. benzoyl peroxide or azobisisobutyronitrile The process may conveniently be carried out by using an excess of the compound of formula V as a diluent, at temperatures in the range 50° C. to 150° C., preferably 80 to 120° C. for periods of from 1 to 20 hours, optionally in a sealed system and under the autogenic pressure of the reaction.

A particularly useful compound of formula VIII is ethyl 3,3-dimethvl-pent-4-enoate, although other lower alkyl esters may also be used.

The ester of 3,3-dimethylpent-4-enoic acid represented by formula VIII may be replaced by other compounds in which the carboxylate function is replaced by an equivalent function, by which we mean a functional group which does not interfere with the process set out hereinabove but which may subsequently be chemically modified by oxidation or hydrolysis to give the carboxylic acid, for example the nitrile, acetyl, or formyl group. Alternatively the compound of formula VIII may be replaced by a compound of formula:

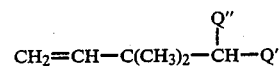

where Q' is selected from alkoxycarbonyl, cyano and acetyl and Q'' is cyano or alkoxycarbonyl.

A yet further process by which the compounds of formula II wherein Q is alkoxy may be prepared involved the reaction of a diene of formula V with an alkyl malonate in the presence of a reducible copper salt, and optionally in the presence of another salt selected from halides of Group I and Group II metals such as lithium chloride or calcium chloride. The initial product which has the formula:

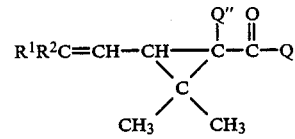

wherein $R^1$, and $R^2$, and Q'' have the meanings given above and Q is alkoxy, may be converted to the required products of formula II by conventional hydrolytic and esterification procedures.

Examples of compounds of formula IX useful in the above processes include hexafluoroethane, chloropentafluoroethane, 1,1-dichlorotetrafluoroethane, 1,2-dichlorotetrafluoroethane, 1,1,1-trichlorotrifluoroethane, 1,1,2-trichlorotrifluoro ethane, 1,1,1-tribromotrifluoroethane, 1,1,1,3-tetrachlorotetrafluoropropane and 1,1,3-trichloropentafluoropropane.

When the various processes for the preparation of the intermediates of formula II are carried out the products are usually mixtures of the various geometrical isomers. Thus the processes may lead to a mixture of cis and trans isomers, often with one form predominating, and, in the cases where $R^1$ is not the same as $R^2$, Z- and E-isomers of both cis and trans forms, again often with one form predominating.

Unless these forms are separated by some physical process, e.g. fractional crystallisation of the carboxylic acids, the final products of formula I will also consist of mixtures of the various isomers, containing more than one of the compounds of Table 1. Typical examples of insecticidally active products, most of which are mixtures of more than one compound, which have been obtained include those set out hereinbelow.

Product no 1 : A mixture of 1 part of compound no 1 with 4 parts of compound no 2.

Product no 2 : A mixture of 1 part of compound no 1 with 1 part of compound no 2.

Product no 3 : Compound no 2 alone.

Product no 4 : Compound no 1 alone.

Product no 5 : A mixture of 19 parts of compound no 31 with 1 part of compound no 32.

Product no 6 : A mixture of 19 parts of compound no 31, 1 part of compound no 32, 19 parts of compound no 33, and 1 part of compound no 34.

Product no 7 : A mixture of 11 parts of compound no 3 with 14 parts of compound no 4.

Product no 8 : A mixture of compounds nos 15, 16, 17 and 18 (composition undetermined).

Product no 9 : A mixture of 1 part of compound no 39 with 1 part of compound no 41.

Product no 10 : A mixture of 19 parts of compound no 43, 1 part of compound no 44, 19 parts of compound no 45 and 1 part of compound no 46.

Product no 11 : A mixture of 19 parts of compound no 43 with 1 part of compound no 44.

Product no 12: A mixture of 19 parts of compound no 39 with 1 part of compound no 40.

Product no 13 : A mixture of 1 part of compound no 19, 9 parts of compound no 2C, 1 part of compound no 21 and 9 parts of compound no 22.

Product no 14 : A mixture of 1 part of compound no 23, 9 parts of compound no 24, 1 part of compound no 25 and 9 parts of compound no 26.

Product no 15 : A mixture of 1 part of compound no. 47 with 1 part of compound no 48.

Product no 16 : Compound no 47.

Product no 17 : A mixture of 1 part of compound no 49 with 1 part of compound no 50.

Product no 18 : A mixture of 1 part of compound no 1 with with 2 parts of compound no 2.

Product no 19 : A mixture of 3 parts of compound no 5 with 2 parts of compound no 6.

Product no 20 : A mixture of 3 parts of compound no 7 with 2 parts of compound no 8.

Product no 21 : A mixture of 9 parts of compound no 35, 1 part of compound no 36, 6 parts of compound no 37, and 4 parts of compound no 38.

Product no 22 : A mixture of 9 parts of compound no 51 with one part of compound no 52.

Product no 23 : Compound no 53 alone.

Product no 24 : A mixture of 7 parts of compound no 9 with 13 parts of compound no 10.

Product no 25 : A mixture of 7 parts of compound no 11 with 13 parts of compound no 12.

Product no 26 : A mixture undetermined compositions containing compounds 27, 28, 29.and 30.

Product no 27 : A mixture of 10 parts of compound no 54, 1 part of compound no 55, 10 parts of compound no 56 and 1 part of compound no 57.

Product no 28 : A mixture of 10 parts of compound no 58, 1 part of compound no 59, 10 parts of compound no 60 and 1 part of compound no 61.

Product no 29 : A mixture of 2 parts of compound no 13 with 3 parts of compound no 14.

The compounds of formula I may be used to combat and control infestations of insect pests and also other invertebrate pests, for example, acarine pests. The insect and acarine pests which may be combated and controlled by the use of the invention compounds include those pests associated with agriculture (which term includes the growing of crops for food and fiber products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula I suitable inert diluent or carrier materials, and/or surface active agents. The compositions may also comprise another pesticidal material, for example another insecticide or acaricide, or a fungicide, or may also comprise a insecticide synergist, such as for example dodecyl imidazole, safroxan, or piperonyl butoxide.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material for example pumice.

Alternatively the compositions may be in the form of liquid preparations to be used as dips or sprays, which are . generally aqueous dispersions or emulsions of the active ingredient in the presence of one or more known wetting agents, dispersing agents or emulsifying agents (surface active agents.

Wetting agents, dispersing agents and emulsifying agents may be of the cationic, anionic or non-ionic type. Suitable agents of the cationic type include, for example, quaternary ammonium compounds, for example, cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, butylnaphthalene sulphonate, and a mixture of the sodium salts cf diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents. Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydro furfuryl alcohol (THFA).

The compositions to be used as sprays may also be in the form of aerosols wherein the formulation is held in a container under pressure in the presence of a propellant such as fluorotrichloromethane or dichlorodifluoromethane. The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogeneous for a sufficient time to enable them to be applied by conventional spray equipment. The concentrates may contain 10–85% by weight of the active ingredient or ingredients. When diluted to form aqueous preparations, such preparations may contain varying amounts of the active ingredient depending upon the purpose for which they are to be used.

For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of the invention are very toxic to wide varieties of insect and other invertebrate pests, including, for example, the following:

*Aphis fabae* (aphids)
*Megoura viceae* (aphids)
*Aedes aegypti* (mosquitoes)
*Dysdercus fasciatus* (capsids)
*Musca domestica* (houseflies)
*Pieris brassicae* (white butterfly, larvae)
*Plutella maculipennis* (diamond back moth, larvae)
*Phaedon cochleariae* (mustard beetle)
*Telarius cinnabarinus* (carmine spider mite)
*Aonidiella spp.* (scale insects)
*Trialeuroides spp.* (white flies)
*Blattella germanica* (cockroaches)
*Spodoptera littoralis* (cotton leaf worm)
*Chortiocetes terminifera* (locusts)

The compounds of formula I and compositions comprising them have shown themselves to be particularly useful in controlling lepidopteran pests of cotton, for example Spodoptera spp. and Heliothis spp. They are also very useful in combating insect and acarine pests which infest domestic animals, such as *Lucilia sericata*, and ixodid ticks such as Boophilus spp., Ixodes spp., Amblyomma spp., Rhicicephalus spp., and Dermaceutor spp. They are effective in combating both susceptible and resistant strains of these pests in their adult, larval and intermediate stages of growth, and may be applied to the infested host animal by topical, oral or parenteral administration.

The following Examples illustrate the various aspects of the invention.

EXAMPLE 1

This Example illustrates the preparation of 1-chloro1,1-difluoro-2-chlorodifluoromethyl-5-methylhexa-2,4-diene, of formula:

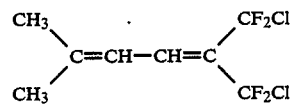

(a) Preparation of 3,3-dimethylallyl triphenylphosphonium bromide.

A mixture of 3,3-dimethylallyl bromide (50.0 g), triphenylphosphine (88.0 g) and dry toluene (500 ml) was stirred and heated at the reflux temperature for one hour, and then kept at the ambient temperature for 18 hours. The white precipitate of 3,3-dimethylall-yl triphenylphosphonium bromide (m.p. 242° C.) was collected by filtration, washed with diethyl ether and dried.

(b) Preparation of 1-chloro-1,1-difluoro-2-chlorodifluoromethyl-5-methylhexa-2,4-diene.

n-Butyl lithium (65.0 ml of a 15% w/w solution in hexane) was slowly added to a vigorously- stirred suspension of 3,3-dimethylallyl triphenylphosphonium bromide (65.0 g) in dry petroleum ether (boiling range 30° C. -40° C., 500 ml) at 0° C. under a nitrogen atmosphere, after which the mixture was kept at the ambient temperature for 18 hours. The mixture was then cooled to 0° C., and 1,3-dichlorotetrafluoroacetone (31.44 g) was added. The mixture was then permitted to attain the ambient temperature over a period of two hours, and the precipitate removed by filtration. The filtrate was concentrated by evaporation, until the volume was about 70 ml, and passed through a short alumina column, after which the remaining solvent was evaporated at atmospheric pressure at a temperature of 69° C. The residual liquid was subjected to fractional distillation, and the fraction boiling at 79° C.-80° C./20 mm Hg collected and identified by infra red an nuclear magnetic resonance spectroscopy as 1-chloro-1,1-difluoro-2-chlorodifluoromethyl-5-methylhexa-2,4-diene.

N.m.r. (CCl$_4$) p.p.m. 1.88–1.94 (m,6H); 6.3 (d,1H); 7.08 (d,1H).

EXAMPLE 2

By similar procedures to that illustrated in Example 1 other dienes were prepared from the appropriate ketones, as follows:

(i) 2-Methyl-5-trifluoromethylhexa-2,4-diene was prepared from 1,1,1-trifluoroacetone.

N.m.r. (CCl$_4$) p.p.m. 1.76–1.82 (m,9H); 5.85–6.00 (m,1H): 6.62–6.78 (m,1H).

(ii) 1,1-Difluoro-2-chlorodifluoromethyl-5-methylhexa2,4-diene was prepared from 1-chloro-1,1,2,2-tetrafluoroacetone.

Infra red (liquid film)—3000, 1650, 1265 cm$^{-1}$.

(iii) 1,1-Difluoro-2-difluoromethyl-5-methylhexa-2,4-diene was prepared from 1,1,3,3-tetrafluoroacetone.

N.m.r. (CCl$_4$) p.p.m. 1.90–2.02 (m,6H); 5.65–7.10 (m,4H).

EXAMPLE 3

This Example illustrates the preparation of 5-hydroxy-2-methyl-6,6,6-trifluoro-5-trifluoromethylhex-2-ene.

A stirred mixture of hexafluoroacetone (235 g) and 3-methylbut-1-ene (100 g) was heated at 125° C. under a pressure of 17 atmospheres for a period of 20 hours. Distillation of the product mixture under reduced pressure yielded 5-hydroxy-2-methyl-6,6,6-trifluoro-5-trifluoromethylhex-2-ene as a mobile colorless liquid, b.p. 43° C./ 15 mm Hg.

N.m.r. (CCl$_4$) p.p.m. 1.77 (d,6H); 2.58-3.00 (m,3H); 5.0-5.4 (m,1H).

EXAMPLE 4

By the use of a procedure similar to that illustrated in Example 3 5-hydroxy-2-methyl-6,6-difluoro-5-trifluoromethylhex-2-ene was prepared from pentafluoroacetone.

N.m.r. (CCl$_4$) p.p.m. 1.78 (d,6H); 2.5-2.75 (m,3H); 5.18 (m,1H); 5.80 (t,1H).

EXAMPLE 5

This Example illustrates the preparation of ethyl (+) cis/trans-3-(2-hydroxy.-3,3,3-trifluoro-2-trifluoromethylprop-1-yl)-2,2-dimethylcyclopropane carboxylate.

A solution of ethyl diazoacetate (9.12 g) in dichloromethane (400 ml) was added dropwise over a period of 48 hours to 5-hydroxy-2-methyl-6,6,6-trifluoro-5-trifluoromethylhex-2-ene (18.9 g) in the presence of a catalytic amount of anhydrous copper (II) sulphate at 110° C.-120° C.

The resultant mixture was washed with water, dried over anhydrous magnesium sulphate, and distilled to yield several fractions within the range 68° C.-90° C. at 0.15 mm. N.m.r., infra red and mass spectral analysis indicated that these fractions consisted principally of the (+)-cis and (+)-trans-isomers of ethyl 3-(2-hydroxy-3,3,3-trifluoro-2- trifluoromethylprop-1-yl)-2,2-dimethylcyclopropane carboxylate in different proportions.

N.m.r. (CDCl$_3$) p.p.m. 1.04-1.40 (m,9H); 1.55-2.43 (m,4H); 4.00-4.37 (m,2H).

EXAMPLE 6

By the use of a procedure similar to that illustrated in Example 5 5-hydroxy-2-methyl-6,6-difluoro-5-trifluoromethylhex-2-ene was converted to ethyl (+)-cis/trans-3-(2-hydroxy-3,3-difluoro-2-trifluoromethylprop-1-yl)-2,2-dimethyl-cyclopropane carboxylate.

N.m.r. (CCl$_4$) p.p.m. 1.3-2.4 (m,13H); 4.0-4.35(m,2H); 4.6-4.8 (m,1H); 5.2-6.4 (m,1H).

EXAMPLE 7

This Example illustrates the preparation of ethyl (+)-cis/trans-3(3,3,3-trifluoro-2-trifluoromethylprop-1-en-1-yl)-2,2-dimethylcyclopropane carboxylate.

A mixture of ethyl (+)-cis/trans-3-(2-hydroxy-3,3,3-trifluoro-2-trifluoromethylprop-1-yl)-2,2-dimethylcyclopropane carboxylate (4.62 g), phosphorus oxychloride (2.2 g), and dry pyridine (5.3 ml) was heated at 110° C. for a period of 65 hours, after which it was poured into iced water and stirred for 5 hours. The mixture thus obtained was extracted with diethyl ether, and the extracts washed with water and dried over anhydrous sodium sulphate. After removal of the ether by evaporation under reduced pressure the residual oil was distilled under reduced pressure, and ethyl (+)-cis/trans-3-(3,3,3-trifluoro- 2-trifluoromethylprop-1-en1-yl)-2,2-dimethylcyclopropane carboxylate was obtained as a colourless oil, b.p. 60° -65°/0.5 mm Hg.

N.m.r. (CDCl$_3$) p.p.m. 1.15-1.39 (m,9H); 1.75-2.60 (m,2H); 4.02-4.34 (m,2H); 6.36 and 7.36 (dd,1H).

EXAMPLE 8

By the use of a procedure similar to that illustrated in Example 7 ethyl (+)-cis/trans-3-(3,3-difluoro-2-trifluoromethylprop-1-en-1-yl)-2,2-dimethylcyclopropane carboxylate was obtained from the product of Example 6.

N.m.r (CCl$_4$) p.p.m. 1.2-1.4 (m,9H); 1.6-2.6 (m,2H); 4.0-4.4 (m,2H); 5.4-7.2 (m,2H).

EXAMPLE 9

By the use of similar procedures to that illustrated in Example 5 the following ethyl esters of formula II were obtained from the stated dienes by reaction with ethyl diazoacetate.

(i) Ethyl (+)-cis/trans-3-(3,3-difluoro-2-difluoromethylprop-1-en-1-yl)-2,2-dimethylcyclopropane carboxylate, from 1,1-difluoro-2-difluoromethyl-5-methylhexa-2,4-diene.

N.m.r. (CCl$_4$) p.p.m. 1.25-1.44 (m,9H); 1.60-2.40 (m,2H); 4.0-4.30 (m,2H); 5.58-7.34 (complex, 3H).

(ii) Ethyl (+)-cis/trans-3-(E/Z-2-trifluoromethylprop-1-en-1-yl)-2,2-dimethylcyclopropane carboxylate, from 2-trifluoromethyl-5-methylhexa-2,4-diene.

N.m.r (CCl$_4$) p.p.m. 1.10-1.40 (m,9H); 1.50-2.10 (m,5H); 4.0-4.38 (m,2H); 5.24-6.46 (m,1H).

(iii) Ethyl (+)-cis/trans-3-(3-chloro-3,3-difluoro-2-chlorodifluoromethylprop-1-en-1-yl)-2 2-dimethylcyclopropane carboxylate, from 1-chloro-1,1-difluoro-2-chlorodifluoromethyl-5-methylhexa-2,4diene.

N.m.r. (CCl$_4$) p.p.m. 1,28-1.42 (m,9H); 1.78-2.60 (m,2H); 4.08-4.26 (m,2H); 6.20 and 7.16 (dd, 1H).

(iv) Ethyl (+)-cis/trans-3- (E/Z-3,3-difluoro-2-chlorodifluoromethylprop-1-en-1-yl)-2,2-dimethylcyclopropane carboxylate, from 1,1-difluoro-2-chlorodifluoromethyl-5-methylhexa-2,4-diene.

N.m.r. (CCl$_4$) p.p.m. 1.24-1.52 (m,9H); 1.64-2.50 (m,2H); 3.90-4.30 (m,2H); 5.50-7.04 (m,2H).

EXAMPLE 10

This Example illustrates the preparation of ethyl 3,3-dimethyl-4,6,6-trichloro-7,7,7-trifluoroheptanoate, of formula:

$$CF_3CCl_2CH_2CHClC(CH_3)_2CH_2CO_2C_2H_5$$

A mixture of ethyl 3,3-dimethylpent-4-enoate (7.0 g), 1,1,1-trichloro-2,2,2-trifluoroethane (20.0 g) and benzoyl peroxide (0.1 g) was heated in a sealed glass tube for 5 hours at 100° C. The mixture obtained was carefully distilled and ethyl 3,3-dimethyl-4,6,6-trichloro-7,7,7-trifluoroheptanoate was collected as a fraction boiling at 112° C.-114° C./ 2 mm Hg, and its identity confirmed by infra red and nuclear magnetic spectroscopic analysis.

EXAMPLE 11

By the use of procedures similar to that set out in Example 10 certain other halogenated esters were prepared by reacting haloalkanes with ethyl 3,3-dimethylpent-4-enoate as follows:

(i) Ethyl 3,3-dimethyl-7,7-difluoro-4,6,6,7-tetrachloroheptanoate from 1,1-difluorotetrachloroethane.

N.m.r. (CDCl$_3$) p.p.m. 1.10–1.35 (m,9H); 2.10–3.00 (m,4H); 4.12 (q,2H); 4.52 (dd,1H).

(ii) Ethyl 3,3-dimethyl-6,7,7-trifluoro-4,6,7-trichloroheptanoate from 1,1,2-trifluorotrichloroethane. The boiling point of the product was 75° C.–76° C./0.05 mm Hg.

(iii) Ethyl 3,3-dimethyl-4,6,6-tribromo-7,7,7-trifluoroheptanoate from 1,1,1-tribromotrifluoroethane.

N.m.r. (CDCl$_3$) p.p.m. 1.16–1.44 (m,9H); 2.50 (q,2H); 3.04 (q,2H); 4.18 (q,2H); 4.60–4.74 (m,1H).

(iv) Ethyl 3,3-dimethyl-7,7,8,8,8-pentafluoro-4,6,6-trichlorooctanoate from 1,1,1-trichloropentafluoropropane.

N.m.r. (CCl$_4$) p.p.m. 1.13–1.40 (m,9H); 2.14–2.92 (m,4H); 3.96–4.25 (q,2H); 4.5–4.62 (m,1H).

(v) Ethyl 3,3-dimethyl-7,7,8,8-tetrafluoro-4,6,6,8tetrachlorooctanoate from 1,1,1,3-tetrachlorotetrafluoropropane.

EXAMPLE 12

This example illustrates the preparation of ethyl (+)-cis/trans-3 (E/Z-2-chloro-3,3,3-trifluoroprop-1-en-1-yl)-2,2-dimethylcyclopropane carboxylate.

The ethyl 3,3-dimethyl-4,6,6-trichloro-7,7,7-trifluoroheptanoate obtained in Example 10 was dissolved in dry tetrahydrofuran (30 ml) and the solution added dropwise to a suspension of sodium t-butoxide (2.75 g, prepared in situ from sodium hydride and t-butyl alcohol) in dry tetrahydrofuran (120 ml) at 0° C. When the addition was complete the mixture was stirred for a period of 2 hours at 0° C. and then acidified with ethanolic hydrogen chloride. After diluting the mixture with diethyl ether it was washed with water, dried over anhydrous magnesium sulphate and concentrated by evaporation of the solvents under reduced pressure. The residual yellow oil was carefully distilled under reduced pressure to yield ethyl (+)-cis/trans-3-(2-chloro-3,3,3-trifluoroprop-1-en-1-yl)-2,2-dimethylcyclopropane carboxylate, b.p. 70° C./0.5 mm Hg. Nuclear magnetic resonance analysis indicated that the product consisted of a mixture of about 60% of the cis-isomers and about 40% of the trans-isomers (across the cyclopropane ring), there being in each case about 90–95% of the isomer in which the trifluoromethyl group is trans to the cyclopropane ring on the double bond (the Z-isomer), and about 5–10% of the isomer in which it is cis (the E-isomer).

EXAMPLE 13

By the use of procedures similar to that illustrated in Example 12 other ethyl esters of formula II were prepared as follows:

(i) Ethyl (+)-cis/trans-3-(E/Z-2,3-dichloro-3,3-difluoroprop-1-en-1-yl)-2,2-dimethylcyclopropane carboxylate, from ethyl 3,3-dimethyl-7,7-difluoro-4,6,6,7-tetrachloroheptanoate.

N.m.r. (CDCl$_3$) p.p.m. 1.15–1.55 (m,9H); 1.55–2.50 (m,2H); 4.00–4.33 (m,2H); 6.13 and 6.95 (dd,1H).

(ii) Ethyl (+)-cis/trans-3-(E/Z-3-chloro-2,3,3-trifluoroprop-1-en-1-yl)-2,2-dimethylcyclopropane carboxylate, from ethyl 3,3-dimethyl-6,7,7-trifluoro-4,6,7-trichloroheptanoate.

N.m.r. (CCl$_4$) p.p.m. 1.20–1.58 (m,9H); 1.58–2.33 (m,2H); 4.15 (q,2H); 5.10, 5.41, 5.91 and 6.25 (4d,1H).

(iii) Ethyl (+)-cis/trans-3-(2-bromo 3,3,3-trifluoroprop1-en-1-yl)-2,2-dimethylcyclopropane carboxylate, from ethyl 3,3-dimethyl-4,6,6-tribromo-7,7,7trifluoroheptanoate.

N.m.r. (CCl$_4$) p.p.m. 1.10–1.40 (m,9H); 1.60–2.44 (m,2H); 3.96–4.28 (m,2H); 5.96–7.26 (m,1H).

(iv) Ethyl (+)-cis/trans-3-(2-chloro-3,3,4,4,4-pentafluorobut-1-en-1-yl)-2,2-dimethylcyclopropane carboxylate from ethyl 3,3-dimethyl-7,7,8,8,8-pentafluoro-4,6,6-trichlorooctanoate.

N.m.r. (CCl$_4$) p.p.m. 1.15–2.53 (complex,11H); 92–4.30 (m,2H); 6.12 and 6.92 (dd,1H).

(v) Ethyl (+)-cis/trans-3-(2,4-dichloro-3,3,4,4-tetrachlorobut-1-en-1-yl-)-2,2 dimethylcyclopropane carboxylate, from ethyl 3,3-dimethyl-7,7,8,8- tetrafluoro-4,6,6,8-tetrachlorooctanoate.

EXAMPLE 14

This Example illustrates the preparation of (+)-cis/trans-3-(3,3,3-trifluoro-2-trifluoromethyl-prop-1-en-1-yl) -2,2-dimethylcyclopropane carboxylic acid.

A mixture of ethyl (+)-cis/trans-3-(3,3,3-trifluoro-2-trifluoromethylprop-1-en-1-yl)-2,2-dimethylcyclopropane carboxylate (0.52 g), glacial acetic acid (2.52 ml), hydrobromic acid (48% w/v; 3.36 ml), and water (1.12 ml) was heated at the reflux temperature for a period of 10 hours. After cooling the mixture it was diluted with water (50 ml) and extracted several times with diethyl ether. The extracts were combined, washed with water, dried over anhydrous sodium sulphate, and concentrated by evaporation of the ether under reduced pressure. The residual oil was shown by spectroscopic analysis to consist principally of (+)-cis/trans-3-(3,3,3-trifluoro-2-trifluoromethylprop-1-en-1-yl)-2,2-dimethylcyclopropane carboxylic acid.

EXAMPLE 15

This Example illustrates the conversion of (+)-cis/trans-3-(3,3,3-trifluoro-2-trifluoromethylprop-1-en-1 yl)-2,2-dimethylcyclopropane carboxylic acid to its acid chloride.

A mixture of (+)-cis/trans-3-(3,3,3-trifluoro-2-trifluoromethyl-prop-1-en-1-yl)-2,2-dimethylcyclopropane carboxylic acid (0.4 g) and thionyl chloride (5.0 ml) was heated at the reflux temperature for a period of 2 hours, after which the excess thionyl chloride was removed by distillation under reduced pressure, leaving (+)-cis/trans-chlorocarbonyl-3-(3,3,3-trifluoro-2-trifluoromethyl-prop-1-en-1-yl)-2,2-dimethylcyclopropane.

EXAMPLE 16

This Example illustrates the preparation of (+)-α-cyano-3-phenoxybenz-yl (+)-cis/trans-3-(3,3,3-trifluoro-2-trifluoromethylprop-1-en-1-yl)-2,2-dimethyl cyclopropane carboxylate, herein referred to as Product no 1.

To the residue of (+)-cis/trans-1-chlorocarbonyl-3(3,3,3-trifluoro-2-trifluoromethylprop-1-en-1-yl)-2,2-dimethylcyclopropane (obtained in Example 15) was added a mixture of pyridine (0.12 g) and (+)-α-cyano-3-phenoxybenzyl alcohol (0.33 g) and the mixture thus obtained was stirred for a period of 16 hours at the ambient temperature. Water (20 ml) was added and the mixture extracted with diethyl ether (3×10 ml). The combined extracts were washed with water, saturated sodium bicarbonate solution, and water and dried over anhydrous sodium sulphate After removal of the ether by evaporation under reduced pressure the residual oil was subjected to preparative thick-layer chromatography, using 2 mm thick silica on glass with chloroform as eluent, to yield (+)-α-cyano-3-phenoxybenzyl (+)-cis/trans-3-(3,3,3-trifluoro-2-trifluoromethylprop-1-en-1-yl)-2,2-dimethylcyclopropane carboxylate (Rf 0.53), containing about 20% of the cis-isomer and about 80% of the trans-isomer. Spectral data: infra red, 1755, 1680, 1600, 1490, 1300, 1160; n.m.r., 0.9–2.5τ, 6.0–6.15τ, 6.35–7.2τ; mass spectrum, M+ 483(275, 259, 231, 209, 208, 181).

EXAMPLE 17

This Example illustrates the preparation of (+)-cis/trans-3-(2 chloro-3,3,3 trifluoroprop-1-en-1-yl)-2,2-dimethylcyclopropane carboxylic acid.

A mixture of ethyl (+)-cis/trans-3-(2-chloro-3,3,3-trifluoro-prop-1-en-1-yl)-2,2-dimethylcyclopropane carboxylate (0.52 g), glacial acetic acid (2.52 ml), hydrobromic acid (48% w/v; 3.36 ml), and water (1.12 ml) was heated at the reflux temperature for a period of 10 hours. After cooling the mixture it was diluted with water (50 ml) and extracted several times with diethyl ether. The extracts were combined, washed with water, dried over anhydrous sodium sulphate, and concentrated by evaporation of the ether under reduced pressure. The residual oil was shown by spectroscopic analysis to consist principally of (+)-cis/trans-3-(2-chloro-3,3,3-trifluoroprop-1-en-1-yl)-2,2-dimethylcyclopropane carboxylic acid.

EXAMPLE 18

This Example illustrates the conversion of (+)-cis/-trans-3-(2-chloro 3,3,3-trifluoroprop-1-en-1-yl)-2,2-dimethylcyclopropane carboxylic acid to its acid chloride.

A mixture of (+)-cis/trans-3-(2-chloro-3,3,3-trifluoroprop-1-en-1-yl)-2,2-dimethylcyclopropane carboxylic acid (0.4 g) and thionyl chloride (5.0 ml) was heated at the reflux temperature for a period of 2 hours, after which the excess thionyl chloride was removed by distillation under reduced pressure, leaving (+)-cis/-trans-1-chlorocarbonyl-3-(2-chloro-3,3,3-trifluoroprop-1-en-1-yl)-2,2-dimethylcyclopropane.

EXAMPLE 19

This Example illustrates the preparation of (+)-α-cyano-3-phenoxybenzyl (+)-cis/trans-3-(2-chloro-3,3,3-trifluoroprop-1-en-1-yl)-2,2-dimethyl cyclopropane carboxylate, herein referred to as product no 6.

To the residue of (+)-cis/trans-1-chlorocarbonyl-3-(2-chloro-3,3,3-trifluoroprop-1-en-1-yl)-2,2-dimethylcyclopropane (obtained in Example 18) was added a mixture of pyridine (0.12 g) and (+)-α-cyano-3-phenoxybenzyl alcohol (0.33 g) and the mixture thus obtained was stirred for a period of 16 hours at the ambient temperature. Water (20 ml) was added and the mixture extracted with diethyl ether (3×10 ml). The combined extracts were washed with water, saturated sodium bicarbonate solution, and water and dried over anhydrous sodium sulphate. After removal of the ether by evaporation under reduced pressure the residual oil was subjected to preparative thick-layer chromatography, using 2 mm thick silica on glass with chloroform as eluent, to yield (+)-α-cyano-3-phenoxybenzyl (+)-cis-3-(2-chloro3,3,3-trifluoroprop-1-en-1-yl)-2,2-dimethylcyclopropane carboxylate (Rf 0.52), and the corresponding trans isomers (Rf 0.42), each containing about 90–95% of the Z-isomer. Spectral data : infra red (CHCl3) 1740, 1660, 1590, 1480, 1460 cm−1; n.m.r. (CCl4): 6.90–7.50 τ, 1.60–2.70 τ, 1.50–1.00 96 , and specific peaks at 6.3 τ(benzylic H), 6.85, 6.50, 6.11 and 5.84 τ (vinylic H) tentatively assigned to the Z-cis, E-cis, Z-trans and E-trans isomers respectively.

EXAMPLE 20

By the use of procedures similar to those illustrated in Example 14 and Example 17 the following carboxylic acids were prepared from the corresponding ethyl esters.

(i) (+)-cis/trans-3-(3,3-difluoro-2-trifluoromethyl-prop-1-en-1-yl)-2,2-dimethylcyclopropane carboxylic acid.

Infra red (liquid film) 3500–2400, 1700, 1665 cm−1.

(ii) (+)-cis/trans-3-(3,3-difluoro-2-difluoromethyl-prop-1-3n-1-yl)-2,2-dimethylcyclopropane carboxylic acid.

(N.m.r. (CCl4) p.p.m. 1.30–1.50 (m,6H); 1.70–2.60 (complex, 2H); 5.70–7.13 (complex, 3H).

(iii) (+)-cis/trans-3-(E/Z-2-trifluoromethylprop-1-en1-yl)-2,2-dimethylcyclopropane carboxylic acid.

N.m.r. (CCl4) p.p.m. 1.22–1.44 (m,6H); 1.6–2.3 (m,5H); 5.36–6.6 (m,1H); 11.9 (s,1H).

(iv) (+)-cis/trans-3-(3-chloro-3,3-difluoro-2-chlorodifluoromethylprop-1-en-1-yl)-2,2-dimethylcyclopropane carboxylic acid.

N.m.r. (CCl4) p.p.m. 1.24–1.42 (m,6H); 1.80–2.68 (m,2H); 6.16 and 7.12 (dd,1H); 11.6 (s,1H).

(v) (+)-cis/trans-3-(E/Z-3,3-difluoro-2-chlorodifluoromethylprop-1-en-1-yl)-2,2-dimethylcyclopropane carboxylic acid.

Infra red (CHCl3) 3450–2500, 1705, 1675 cm−1.

(vi) (+)-cis/trans-3-(2-bromo-3,3,3-trifluoroprop-1-en1-yl)-2,2-dimethylcyclopropane carboxylic acid.

Infra red (CHCl3) 3400–2450, 1700, 1650, 1275, 1140 cm−1.

(vii) (+)-cis/trans-3-(3-chloro-2,3,3-trifluoroprop-1-en-1-yl)-2,2-dimethylcyclopropane carboxylic acid.

Infra red (oil film) 3400–2200, 1700, 1450, 1140, 1070 cm−1.

(viii) (+)-cis/trans-3-(2,3-dichloro-3,3-difluoroprop-1- en-1-yl)-2,2-dimethylcyclopropane carboxylic acid.

Infra red (CHCl3) 3400–2200, 1700 cm−1.

(ix) Pure (+)-cis-3-(2,3-dichloro-3,3-difluoroprop-1-en-1-yl)-2,2-dimethylcyclopropane carboxylic acid was precipitated on cooling from a concentrated solution of the mixed cis and trans acids in hexane.

N.m.r. (CDCl3) p.p.m. 1.25 (s,6H); 1.80–2.25 (m,2H); 6.73 (d,1H).

(x) (+)-cis/trans-3-(2-chloro-3,3,4,4,4-pentafluorobut-1-en-1-yl)-2,2-dimethylcyclopropane carboxylic acid.

N.m.r. (CDCl3) p.p.m. 1.10–1.50 (m,6H); 1.68–2.58 (m,2H); 6.14 and 6.85 (dd,1H).

(xi) (+)-cis/trans-3-(2,4-dichloro-3,3,4,4-tetrafluorobut-1-en-1-yl)-2,2-dimethylcyclopropane carboxylic acid.

EXAMPLE 21

The various carboxylic acids of Example 20 were convert to the insecticidal ester products according to formula I by reacting the acid chlorides with 3-phenoxybenzyl alcohol, (+)-α-cyano-3-phenoxybenzyl alcohol or (+)-α-ethynyl-3-phenoxybenzyl alcohol. The products of these reactions (herein designated Product nos 2 to 5 and 7 to 29) are for the most part mixtures of more than one of the compounds of Table I, as set out hereinbelow.

Product no 2 :
(+)-α-cyano-3-phenoxybe-nzyl (+)-cis/ trans-3 (3,3,3-trifluoro-2-trifluoromethylprop-1-en-1-yl)-2,2-dimethyl cyclopropane carboxylate, is a mixture of 1 part of compound no 1 with 1 part of compound no 2.

N.m.r. (CCl4) p.p.m. 1.20-1.40 (m,6H); 1.80-2.30 (m,2H); 6.17-6.37 and 6.85-7.42 (mm,llH).

Product no 3 :
(+)-α-cyano-3-phenoxybenzyl (+)-trans-3-(3,3,3-trifluoro-2 trifluoromethylprop-1-en-1-y-1)-2,2-dimethyl-cyclopropane carboxylate, is compound no 2 alone.

Product no 4 :
(+)-α-cyano-3-phenoxybenzyl (+)-cis-3-(3,3,3-trifluoromethylprop-1-en-1-yl)-2,2-dimethylcyclopropane carboxylate, is compound no 1 alone.

Product no 5 :
(+)-α-cyano-3-phenoxybenzyl (+)-cis-3-(2-chloro-3,3,3-trifluoroprop-1-en-1-yl)-2,2-dimethylcyclopropane carboxylate, is a mixture of 19 parts of compound no 31 with 1 part of compound no 32.

Product no 7 :
3-phenoxybenzyl (+)-cis/trans-3-(3,3,3-trifluoro-2-trifluoromethylprop-1-en-1yl)-2,2-dimethylcyclopropane carboxylate, is a mixture of 11 parts of compound no 3 with 14 parts of compound no 4.

N.m.r. (CCl4) p.p.m. 1.18-1.40 (m,6H); 6.70-7.40 (dm,lOH).

Product no 8 :
(+)-α-cyano-3-phenoxybenzyl (+)-cis/ trans-3-(3,3-difluoro-2-trifluoromethylprop-1-en-1-yl)-2,2-dimethyl-cyclopropane carboxylate, is a mixture of compounds nos 15, 16, 17 and 18 (composition undetermined).

Infra red (liquid film) 1745, 1665, 1595 cm$^{-1}$.

Product no 9 :
3-phenoxybenzyl (+)-cis/trans-3-(Z-2,3-dichloro-3,3-difluoroprop-1-en-1-yl)-2,2-dimethylcyclopropane carboxylate is a mixture of 1 part of compound no 39 with 1 part of compound no 41.

N.m.r. (CDCl3) p.p.m. 1.20-1.37 (m,6H); 1.73-2.50 (m,2H); 5.10 (d,2H); 6.12 and 6.88-7.48 (dm,lOH).

Product no 10 :
(+)-α-cyano-3-phenoxybenzyl (+)-cis/ trans-3-(Z/E-2,3-dichloro-3,3-difluoro-prop-1-en1-yl)2,2-dimethylcyclopropane carboxylate is a mixture of 19 parts of compound no 43, 1 part of compound no 44, 19 parts of compound no 45 and 1 part of compound no 46.

N.m.r. (CCl4) p.p.m. 1.18-1.45 (m,6H); 1.73-2.50 (m,2H); 6.32 (m,lH); 6.08 and 6.81 (dd,lH); 6.90-7.44 (m,9H).

Product no 11 :
(+)-α-cyano-3-phenoxybenzyl (+)-cis-3-(Z/E-2,3-dichloro-3,3-difluoroprop1-en-1-yl)-2,2-dimethylcyclopropane carboxylate is a mixture of 19 parts of compound no 43 with 1 part of compound no 44.

N.m.r. (CCl4) p.p.m. 1.18-1.40 (m,6H); 1.92-2.32 (m,2H); 6.31 (d,lH); 6.81 (d,lH); 6.90-7.45 (m,9H).

Product no 12 :
3-phenoxybenzyl (+)-cis-3-(Z/E-2,3dichloro-3,3-difluoroprop-1-en-1-yl)2,2-dimethylcyclopropane carboxylate, is a mixture of 19 parts of compound no 39 with 1 part of compound no 40.

N.m.r. (CCl4) p.p.m. 1.05-1.48 (m,6H); 1.84-2.38 (m,2H); 5.02 (s,2H); 6.72-7.45 (m,lOH).

Product no 13 :
(+)-α-cyano-3-phenoxybenzyl (+)-cis/ trans-3-(Z/E-2-trifluoromethylprop-1en-1-yl)-2,2-dimethylcy-cyclopropane carboxylate is a mixture of 1 compound no 19, 9 parts of compound no 20, 1 part of compound no 21 and 9 parts of compound no 22.

N.m.r. (CCl4) p.p.m. 1.22-1.40 (m,6H); 1 60-2.30 (m,5H); 5.2-6.45 (mlH).

Product no 14 :
3-phenoxybenzyl (+)-cis/trans-3- (Z/E-2-trifluoromethylprop-1-en-1-yl)-2,2-dimethylcyclopropane carboxylate is a mixture of 1 part of compound no 23, 9 parts of compound no 24, 1 part of compound no 25 and 9 parts of compound no 26.

N.m.r. (CCl4) p.p.m. 1.22-1.40 (m,6H); 1.58-2.2 (m,5H); 5.02 (s,2H); 5.2-6.45 (m,lH); 6.85-7.42 (m,9H).

Product no 15 :
(+)-α-3-phenoxybenzyl (+)-cis/ trans-3-(Z-3-chloro-2,3,3-trifluoroprop-1-en-1-yl)-2,2-dimethyl cyclopropane carboxylate, is a mixture of 1 part of compound no 47 with 1 part of compound no 48.

N.m.r. (CCl4) p.p.m. 1.15-1.40 (m,6H); 1.65-2.40 (m,2H); 5.08, 5.39, 5.80 and 6.12 (4d,lH); 6.35 (m,lH); 6.92-7.50 (m,9H).

Product no 16 :
(+)-α-cyano-3-phenoxybenzyl (+)-cis-3-(Z-3-chloro-2,3,3-trifluoroprop-1en-1-yl) 2,2-dimethylcyclopropane carboxylate, is compound no 47.

N.m.r. (CCl4) p.p.m. 1.18-1.40 (m,6H); 1.85-2.33 (m,2H); 5.80 and 6.11 (dd,lH); 6.35 (d,lH); 6.95-7.60 (m,9H).

Product no 17 :
3-phenoxybenzyl (+)-cis,/trans-3-(Z-3-chloro-2,3,3-trifluoroprop-1-en-1yl)-2,2-dimethylcyclopropane carboxylate, is a mixture of 1 part of compound no 49 with 1 part of compound no 50.

N.m.r. (CCl4) p.p.m. 1.15-1.30 (m,6H): 1.65-2.40 (m,2H); 5.10, 5.40, 5.92 and 6.23 (m,3d,3H); 6.90-7.45 (m,9H).

Product no 18 :
(+)-α-cyano-3-phenoxybenzyl (+)-cis/ trans-3-(3,3,3-trifluoro-2-trifluoromethylprop-1-en-1-yl)-2,2-dimethylcyclopropane carboxylate, is a mixture of 1 part of compound no 1 with 2 parts of compound no 2.

Product no 19 :
3-phenoxybenzyl (+)-cis/trans-3-(3,3-difluoro 2-difluoromethylprop-1-en-1yl)-2,2-dimethylcyclopropane carboxylate is a mixture of 3 parts of compound no 5 with 2 parts of compound no 6.

N.m.r. (CCl4) p.p.m. 1.18-1.37 (m,6H); 1.60-2.45 (m,2H); 5.03-5.1 (m,2H); 5.13 7.47 (complex, 12H).

Product no 20 :
(+)-α-cyano-3-phenoxybenzyl (+)-cis/ trans-3-(3,3-difluoro-2-difluoromethylprop-1-en-1-yl)-2,2-dimethyl-cyclopropane carboxylate is a mixture of 3 parts of compound no 7 with 2 parts of compound no 8.

N.m.r. (CCl4) p.p.m. 1.20-1.40 (m,6H); 1.80-2.47 (m,2H); 6.17-6.37 and 6.85-7.43 (mm,13H).

Product no 21 :
3-phenoxybenzyl (+)-cis/trans-3-(Z/E-2-chloro-3,3,3-trifluoroprop-1-en-1-yl)-2,2-dimethylcyclopropane carboxylate, is a mixture of 9 parts of compound no 35, 1 part of compound no 36, 6 parts of compound no 37, and 4 parts of compound no 38.

Product no 22 :
(+)-α-cy-ano-3-phenoxybenzyl (+)-cis/ trans-3-(Z-2,4-dichloro-3,3,4,4-tetrafluorobut-1-en-1-yl)-2,2-dimethylcyclopropane carboxylate, is a mixture of 9 parts of compound no 51 with one part of compound no 52.

Product no 23 :

(+)-α-cyano-3-phenoxybenzyl (+)-trans-3-(Z-2-chloro-3,3,4,4,4-pentafluorobut1-en-1-yl)-2,2-dimethylcyclopropane carboxylate is compound no 53.

N.m.r. (CCl4) p.p.m. 1.16–1.42 (m,6H); 1.74–2.60 (m,2H); 5.98–6.40 and 6.77–7.55 (mm,11H).

Product no 24 :

3-phenoxybenzyl (+)-cis/trans-3-(3-chloro-3,3-difluoro 2-chlorodifluoromethylprop-1-en-1-yl)-2,2-dimethylcyclopropane carboxylate, is a mixture of 7 parts of compound no 9 with 13 parts of compound no 10.

N.m.r. (CCl4) p.p.m. 1.24–1.42 (m,6H); 1.76–2.60 (m,2H); 5.02 (s,2H); 6.16 and 7.12 (dd,1H); 6.76–7.40 (m,9H).

Product no 25 :

(+)-α-cyano-3-phenoxybenzyl (+)-cis/ trans-3(3-chloro-3,3-difluoro-2-chlorodifluoromethylprop-1-en-1-yl)-2,2dimethylcyclopropane carboxylate, is a mixture of 7 parts of compound no 11 with 13 parts of compound no 12.

N.m.r. (CCl4) p.p.m. 1.24–1.42 (m,6H); 1.84–2.70 (m,2H); 6.16 and 7.12 (dd,1H); 6.36 (ss,1H); 6.90–7.50 (m(9H).

Product no 26 :

(+)-α-cyano-3-phenoxybenzyl (+)-cis/ trans-3-(Z/E-3,3-difluoro-2-chlorodifluoromethylprop-1-en-1-yl)-2,2dimethylcyclopropane carboxylate, is a mixture of undetermined composition containing compounds 27, 28, 29 and 30.

N.m.r. (CCl4) p.p.m. 1.24–1.52 (m,6H); 1.76–2.70 (m,2H); 5.6–7.6 (m,12H).

Product no 27 :

(+)-60 -cyano-3-phenoxybenzyl (+)-cis/trans-3-(Z/E-2-bromo-3,3,3-trifluoroprop-1-en-1-yl)-2,2-dimethylcyclopropane carboxylate, is a mixture of 10 parts of compound no 54, 1 part of compound no 55, 10 parts of compound no 56 and 1 part of compound no 57.

N.m.r. (CCl4) p.p.m. 1.24–1.50 (m,6H); 1.75–2.55 (m,2H); 5.96–7.26 (m,1H); 6.36–6.56 (m,1H); 7.0–7.6 (m,9H).

Product no 28 :

(+)-α-ethynyl-3-phenoxybenzyl ( +)-cis/ trans-3-(Z/E-2-chloro-3,3,3-trifluoroprop-1-en-1-yl)-2,2-dimethylcyclopropane carboxylate, is a mixture of 10 parts of compound no 58, 1 part of compound no 59, 10 parts of compound no 60 and 1 part of compound no 61.

N.m.r. (CCl4) p.p.m. 1.16–1.44 (m,6H); 1.64–2.56 (m,3H); 5.7–7.0 (m,1H); 6.28–6.40 (m,1H); 6.70–7.40 (m,9H).

Product no 29 :

(+)-α-ethynyl-3-phenoxybenzyl (+)-cis/ trans-3-(3,3,3-trifluoro-2-trifluoromethylprop-1-en-1-yl)-2,2-dimethylcyclopropane carboxylate, is a mixture of 2 parts of compound no 13 with 3 parts of compound no 14.

N.m.r. (CCl4) p.p.m. 1.16–1.44 (m,6H); 1.76–2.56 (m,3H); 6.12–7.04 (m,1H); 6.24–6.40 (m,1H); 6.76–7.36 (m,9H).

EXAMPLE 22

This Example illustrates the insecticidal properties of (+)-α-cyano-3-phenoxybenzyl (+)-cis/trans-3-(2-chloro-3,3,3-trifluoro-2-trifluoromethylprop-1-en-1-yl)-2,2-dimethylcyclopropane carboxylate (containing 60% cis-isomer) (Product no 6) and (+)-α-cyano-3-phenoxybenzyl (+)-cis/trans-3-((3,3,3-trifluoro-2-trifluoromethylprop-1-en-1-yl)-2,2-dimethylcyclopropane carboxylate (containing 20% cisisomer) (Product no 1) as representative examples of esters according to the invention.

The activity of the products was tested against a variety of insect and other invertebrate pests. Each product was used in the form of liquid preparations, containing in the case of product no 1 1000, 500, 125 and 62.5 p.p.m. and in the case of product no 6, 50, 25, 12.5 and 6.25 p.p.m. by weight of the product. The preparations were made by dissolving the compound in a mixture of solvents consisting of 4 parts by volume of acetone and 1 part by volume of diacetone alcohol. The solutions were then diluted with water containing 0.01% by weight of a wetting agent sold under the trade name "LISSAPOL" NX until the liquid preparations contained the required concentration of the compound. "Lissapol" is a Trade Mark.

The test procedure adopted with regard to each pest was basically the same and comprised supporting a number of the pests on a medium which was usually a host plant or a foodstuff on which the pests feed, and treating either or both the pests and the medium with the preparations.

The mortality of the pests was then assessed at periods usually varying from one to three days after the treatment.

The results of the tests are given below in Tables II and III. In these tables the first column indicates the name of the pest species. Each of the subsequent columns indicates the host plant or medium on which it was supported, the number of days which were allowed to elapse after the treatment before assessing the mortality of the pests, and the results obtained for each of the concentrations given above. The assessment is expressed in integers which range from 0–3.

0 represents less than 30% kill
1 represents 30–49% kill
2 represents 50–90% kill
3 represents over 90% kill A dash (-) indicates that no test was carried out. "Contact test" indicates that both the pests and the medium were treated and "residual test" indicates that the medium was treated before infestation with the pests.

The results for Product no 1 are in Table II and for Product no 6 in Table III.

TABLE II

| PEST SPECIES | SUPPORT MEDIUM | NO. OF DAYS | RATE OF APPLICATION (p.p.m.) | | | |
|---|---|---|---|---|---|---|
| | | | 1000 | 500 | 125 | 62.5 |
| *Tetranychus telarius* red spider mites, adults | French Bean | 3 | 3 | 3 | 3 | 3 |
| *Aphis fabae* (black aphids) | Broad Bean | 2 | 3 | 3 | 3 | 3 |
| *Megoura viceae* (green aphids) | Broad Bean | 2 | 3 | 3 | 3 | 3 |

TABLE II-continued

| PEST SPECIES | SUPPORT MEDIUM | NO. OF DAYS | RATE OF APPLICATION (p.p.m.) | | | |
|---|---|---|---|---|---|---|
| | | | 1000 | 500 | 125 | 62.5 |
| *Aedes aegypti* (mosquito adults) | Plywood | 1 | 3 | 3 | 3 | 3 |
| *Musca domestica* (houseflies - contact test) | Milk/ Sugar | 2 | 3 | 3 | 3 | 3 |
| *Plutella maculipennis* (diamond back moth, larvae) - contact test | Mustard | 3 | 3 | 3 | 3 | 3 |
| *Phaedon cochleariae* (mustard beetle - residual test) | Grain | 3 | 3 | 3 | 3 | 3 |
| *Musca domestica* (houseflies - residual test) | Plywood | 3 | 3 | 3 | 3 | 3 |
| *Calandra granaria* (grain beetles - residual test) | Grain | 3 | 3 | 3 | 3 | — |

TABLE III

| PEST SPECIES | SUPPORT MEDIUM | NO. OF DAYS | RATE OF APPLICATION (p.p.m.) | | | |
|---|---|---|---|---|---|---|
| | | | 50 | 25 | 12.5 | 6.25 |
| *Tetranychus telarius* red spider mites, adults | French Bean | 3 | 2 | 2 | 2 | 1 |
| *Aphis fabae* (black aphids) | Broad Bean | 2 | 3 | 3 | 3 | 3 |
| *Megoura viceae* (green aphids) | Broad Bean | 2 | 3 | 3 | 3 | 3 |
| *Aedes aegypti* (mosquito adults) | Plywood | 1 | 3 | 3 | 2 | 2 |
| *Musca domestica* (houseflies - contact test) | Milk/ Sugar | 2 | 3 | 3 | 3 | 3 |
| *Plutella maculipennis* (diamond back moth, larvae) - contact test | Mustard | 3 | 3 | 3 | 3 | 3 |
| *Phaedon cochleariae* (mustard beetle - residual test) | Grain | 3 | 3 | 3 | 3 | 3 |
| *Musca domestica* (houseflies - residual test) | Plywood | 3 | 3 | 2 | 2 | 0 |

EXAMPLE 23

This Example illustrates the insecticidal properties of the products of Example 21. The tests were conducted under the same conditions as those in Example 22. The results are given in Table IV as the percentage mortality of the pests at one rate of application only for each product.

The symbols used in Table IV have the following meanings.

"P no" indicates "Product no" as defined in Example 21.

"Rate" indicates the concentration expressed in parts per million of the active ingredient in the preparations used in the test.

"A" to "M" indicate the pest species used in the tests, which are as follows:

"A" - *Tetranychus telarius* (red spider mites - adults)
"B" - *Tetranychus telarius* (red spider mites - eggs)
"C" - *Aphis fabae* (black aphids)
"D" - *Megoura viceae* (green aphids)
"E" - *Aedes aegypti* (mosquitoes)
"F" - *Musca domestica* (houseflies) - contact activity
"G" - *Musca domestica* (houseflies) - residual activity
"H" - *Plutella xylostella* - residual activity (3 days)
"I" - *Plutella xylostella* - residual activity (10 days)
"J" - *Phaedon cochleariae* (mustard beetle)
"K" - *Calandra granaria* (grain beetle)
"L" - *Tribolium castaneum* (flour beetle)
"M" - *Spodoptora littoralis* (cotton leaf worm)

An asterisk (*) in the table indicates that in addition to the stated mortality the remaining living insects were all severely affected and would have been expected to die if the duration of the text had been extended.

TABLE IV

| P NO | RATE | A | B | C | D | E | F | G | H | I | J | K | L | M |
|---|---|---|---|---|---|---|---|---|---|---|---|---|---|---|
| 1 | 50 | 50 | 40 | 100 | 100 | 80 | 70 | 0 | 0* | 80 | 0* | 25 | 11 | — |
| 2 | 100 | 100 | 90 | 100 | 100 | 100 | 100 | 60* | 80* | 100 | 60* | 100 | 25 | — |
| 3 | 100 | 100 | 0 | 100 | 100 | 100 | 100 | 20 | 50 | 70 | 0 | 80 | 36 | — |
| 4 | 100 | 90 | 0 | 100 | 100 | 100 | 100 | 100 | 100 | — | 40 | 85 | 54 | — |
| 5 | 50 | — | 100 | 100 | 100 | 100 | 100 | 60 | 100 | — | 80 | 100 | 83* | — |
| 6 | 50 | 60 | 70 | 100 | 100 | 100 | 60* | 100 | 100 | — | 100 | 100 | 19* | — |
| 7 | 100 | 98 | 0 | 100 | 100 | 100 | 90 | 100 | 100 | — | 100 | 69 | 35 | — |
| 8 | 100 | 80 | 0 | 100 | 100 | 100 | 50 | 100 | 80* | 100 | 50* | 21 | 17 | — |
| 9 | 25 | 20 | 0 | 90 | 100 | 37 | 100 | 20 | 100 | — | 0* | — | — | — |
| 10 | 25 | 20 | 0 | 100 | 100 | 25 | 100 | 0 | 20* | 67 | — | 25 | 0 | — |
| 11 | 25 | 20 | 0 | 100 | 100 | 66 | 100 | 0 | 0* | 80 | 0* | — | — | — |

TABLE IV-continued

| P NO | RATE | A | B | C | D | E | F | G | H | I | J | K | L | M |
|---|---|---|---|---|---|---|---|---|---|---|---|---|---|---|
| 12 | 25 | 0 | 0 | 100 | 100 | 33 | 100 | 0 | 100 | — | 0* | 28 | 0 | — |
| 13 | 25 | 50 | 0 | 100 | 100 | 100 | 70* | 0 | 20* | — | 10* | 35 | 0 | 100 |
| 14 | 25 | 0 | 0 | 90 | 90 | 100 | 40 | 0 | 70* | — | 0* | 0 | 0 | 100 |
| 15 | 25 | 60 | 0 | 100 | 100 | 100 | 40 | 0 | 70* | — | 0* | 0 | 0 | 100 |
| 16 | 25 | 20 | 0 | 95 | 40 | 40 | 30* | 0 | 50* | — | 0* | 0 | 0 | 100 |
| 19 | 25 | 20 | 0 | 100 | 100 | 30 | 30* | — | 40* | — | 0* | 0 | 0 | 100 |
| 20 | 25 | 0 | 0 | 95 | 100 | 20 | 50* | 0 | 10* | — | 0* | 0 | 0 | 100 |
| 21 | 50 | 60 | 0 | 100 | 100 | 100 | 90* | 20* | 100 | 100 | 100 | 85 | 100 | 60 |
| 22 | 25 | 50 | 100 | 100 | 100 | 0 | 20* | 0 | 80* | 90 | 80* | 0 | 0 | 20 |
| 23 | 25 | 0 | 0 | 100 | 100 | 0 | 100 | 0 | 100 | — | 50* | 0 | 0 | 0 |
| 26 | 250 | 0 | 0 | 100 | 100 | — | 100 | — | 10 | — | 20 | — | — | 0 |
| 27 | 25 | 99 | 95 | 100 | 100 | — | 100 | — | 100 | — | 100 | — | — | 100 |
| 28 | 50 | 0 | 100 | 100 | 100 | — | 73 | — | 100 | — | 90 | — | — | 100 |
| 29 | 50 | 0 | 100 | 100 | 100 | — | 56 | — | 90 | — | 100 | — | — | 80 |

EXAMPLE 24

This Example illustrates the ixodicidal activity of product no 2 and product no 6 against cattle ticks (*Boophilus microplus*).

A suspension of each of the products was prepared by ball milling 10 parts of the product with 985 parts of water and 5 parts of "Teric" N9 ("Teric" is a Registered Trade Mark and "Teric" N9 is a nonionic surfactant obtained by condensing nonylphenol with ethylene oxide in a molar ratio of 1:9) to give a composition containing 1.0% active ingredient A portion of each of the above suspension was then diluted with water to give compositions containing 0.1% and 0.01% active ingredient.

The efficacy of each of the products against engorged adult female ticks of the "Yeerongpilly" strain was tested by applying a microdrop of the appropriate concentration suspension to each of about twenty of the ticks. After 14 days the mortality count of the adult ticks was assessed by coating the eggs laid by them and the percentage of those eggs which had hatched. The results are given in Table V.

The efficacy of each of the products against larval ticks of the "Yeerongpilly" strain was tested as follows: A sheet of filter paper was soaked in the appropriate concentration suspension and then allowed to dry. The treated paper was converted to the form of an envelope and approximately 100 larval ticks of the "Yeerongpilly" strain were enclosed therein. A mortality count was done on the larval ticks 48 hours after they had been placed in the envelope and the kill rated on a 0-5 scale wherein
0 represents 0-20% kill
1 represents 20-50% kill
2 represents 50-80% kill
3 represents 80-95% kill
4 represents 95-99% kill
5 represents 100% kill The results are given in Table V.

In a further test an emulsion of each of the products was prepared by mixing 25 parts of the compound with 75 parts of cyclohexanone and 25 parts of "Teric" N9 and diluting the mixture with water to provide 10,000 parts by volume of an emulsion. Each of the emulsions so obtained was sprayed, to drip point, onto calves heavily infested with various stages of the resistant "Biarra" strain of cattle tick. The efficacy of each of the products was assessed as follows:

(i) All adult female ticks which were fully engorged at the time of spraying were collected soon after spraying the calves. They were then placed in a Petri dish in an incubator for assessment of mortality based on capacity to lay eggs, and if eggs were laid, the viability of the eggs as shown by hatch of viable larvae. Engorged adults, if any, were also collected at 24 hours and 48 hours after spraying and the same assessment of mortality was made. This assessment is referred to as "Mortality Engorged Adults" and the results are given in Table VI.

(ii) At daily intervals predetermined sampling areas on each calf were inspected for the effect of the active ingredient on the immature adults and nymphs. This assessment was rated on the 0-5 scale defined in Example 3 and is referred to as "Mortality - Immature Adults" and "Mortality - Nymphs". The results are given in Table VI.

The symbol "-" is used to indicate that no engorged adults were present.

In these tests permethrin (3-phenoxybenzyl (+)-cis/trans-3(2,2-dichlorovinyl)-2,2-dimethylcyclopropane carboxylate) was used as a standard.

TABLE V

IN VITRO IXODICIDAL ACTIVITY AGAINST ADULTS AND LARVAE

| PRODUCT | % MORTALITY OF ADULTS | | KILL RATING AGAINST LARVAE | | |
|---|---|---|---|---|---|
| | 1% a.i. | 0.1% a.i. | 1% a.i. | 0.1% a.i. | 0.01% a.i. |
| 2 | 100 | 90 | 5 | 5 | 1 |
| 6 | 100 | 100 | 5 | 5 | 5 |

TABLE VI

IN VIVO IXODICIDAL ACTIVITY AGAINST ENGORGED ADULTS, IMMATURE ADULTS AND NYMPHS

| | | MORTALITY | | |
|---|---|---|---|---|
| PRODUCT | ACTIVE INGREDIENT | ENGORGED ADULTS (%) 24 hr/24 hr/48 hr | IMMATURE ADULTS* | NYMPHS* |
| 2 | 0.05 | —/—/— | 5 | 5 |
| 2 | 0.025 | —/—/— | 5 | 5 |
| 2 | 0.02 | —/—/— | 5 | 4 |
| 2 | 0.01 | —/—/— | 5 | 5 |
| 2 | 0.005 | —/—/— | 5 | 4 |

TABLE VI-continued
IN VIVO IXODICIDAL ACTIVITY AGAINST ENGORGED ADULTS, IMMATURE ADULTS AND NYMPHS

| PRODUCT | ACTIVE INGREDIENT | MORTALITY ENGORGED ADULTS (%) 24 hr/24 hr/48 hr | IMMATURE ADULTS* | NYMPHS* |
|---|---|---|---|---|
| 2 | 0.0025 | —/—/— | 4 | 3 |
| 6 | 0.02 | —/—/— | 5 | 5 |
| 6 | 0.01 | —/—/— | 5 | 5 |
| 6 | 0.005 | —/—/— | 5 | 5/4 |
| 6 | 0.0025 | —/—/— | 5 | 5/4 |
| Permethrin | 0.1 | —/—/— | 5 | 5 |
| Permethrin | 0.05 | —/—/— | 5 | 5 |
| Permethrin | 0.01 | 20/60/— | 3 | 1 |

I claim:
1. A compound of the formula

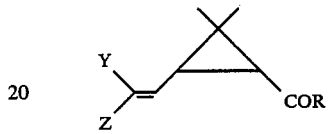

wherein one of Y and Z is a perhaloalkyl group having 1 to 2 carbon atoms and the other is halogen or methyl; and R is $OR^1$ in which $R^1$ represents a phenoxybenzyl group optionally substituted in the alpha position by a cyano or ethynyl group.

* * * * *